(12) United States Patent
 Schmidt

(10) Patent No.: US 11,076,812 B2
(45) Date of Patent: Aug. 3, 2021

(54) METHOD AND DEVICE FOR ASSESSING A MORTALITY RISK OF A CARDIAC PATIENT BASED ON RESPIRATORY SINUS ARRHYTHMIA

(71) Applicant: Georg Schmidt, Munich (DE)

(72) Inventor: Georg Schmidt, Munich (DE)

( * ) Notice: Subject to any disclaimer, the term of this patent is extended or adjusted under 35 U.S.C. 154(b) by 270 days.

(21) Appl. No.: 15/320,165

(22) PCT Filed: Jun. 18, 2015

(86) PCT No.: PCT/EP2015/063740
§ 371 (c)(1),
(2) Date: Dec. 19, 2016

(87) PCT Pub. No.: WO2015/193448
PCT Pub. Date: Dec. 23, 2015

(65) Prior Publication Data
US 2017/0135648 A1 May 18, 2017

(30) Foreign Application Priority Data
Jun. 20, 2014 (EP) .................................... 14002124

(51) Int. Cl.
*A61B 5/024* (2006.01)
*A61B 5/00* (2006.01)
(Continued)

(52) U.S. Cl.
CPC .......... *A61B 5/7275* (2013.01); *A61B 5/0205* (2013.01); *A61B 5/02405* (2013.01);
(Continued)

(58) Field of Classification Search
CPC ... A61B 5/02405; A61B 5/7275; A61B 5/364; A61B 5/352
See application file for complete search history.

(56) References Cited

U.S. PATENT DOCUMENTS 6,305,943 B1 * 10/2001 Pougatchev ........... A61B 5/486
434/238
8,437,837 B2 * 5/2013 Zhou ..................... A61B 5/0452
600/509
(Continued)

OTHER PUBLICATIONS

O'Brien et al. "A Comparison of Algorithms for Estimation of a Respiratory Signal from the Surface Electrocardiogram." Comput Biol Med. Mar. 2007;37(3):305-14. Epub Jun. 13, 2006. (Year: 2006).*
(Continued)

*Primary Examiner* — Meredith Weare
(74) *Attorney, Agent, or Firm* — Workman Nydegger

(57) ABSTRACT

In order to satisfy a need for a high reliability mortality risk prediction method and device while minimizing the efforts to be taken by the patient and health personnel, the present invention provides a method for assessing a mortality risk of a cardiac patient based on respiratory sinus arrhythmia, said method comprising the following steps. Step A: Computing the mean respiratory sinus arrhythmia during inhalation and/or exhalation for a plurality of breathing cycles of said patient. Step B: Assessing the mortality risk of said patient based on said computation. A device for performing said method is also disclosed.

9 Claims, 3 Drawing Sheets

Figure 1:
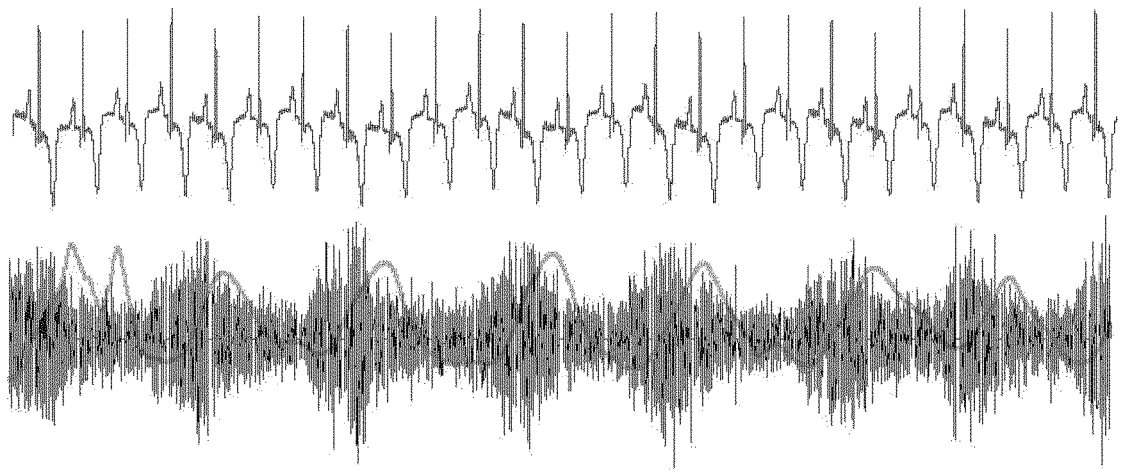

(51) Int. Cl.
*G16H 50/30* (2018.01)
*A61B 5/0205* (2006.01)
*A61B 5/08* (2006.01)
*A61B 5/316* (2021.01)
*A61B 5/352* (2021.01)
*A61B 5/349* (2021.01)

(52) U.S. Cl.
CPC ............ *A61B 5/0816* (2013.01); *A61B 5/316* (2021.01); *A61B 5/352* (2021.01); *G16H 50/30* (2018.01); *A61B 5/024* (2013.01); *A61B 5/08* (2013.01); *A61B 5/349* (2021.01)

(56) References Cited

U.S. PATENT DOCUMENTS

| | | | |
|---|---|---|---|
| 9,380,948 B1 * | 7/2016 | Lo | A61B 5/0205 |
| 2004/0127804 A1 | 7/2004 | Hatlesad | |
| 2006/0167364 A1 * | 7/2006 | Houben | A61B 5/046 |
| | | | 600/515 |
| 2008/0071317 A1 | 3/2008 | Stahmann | |
| 2008/0082133 A1 * | 4/2008 | Zhou | A61B 5/0452 |
| | | | 607/9 |
| 2008/0249439 A1 * | 10/2008 | Tracey | A61H 39/04 |
| | | | 601/46 |
| 2012/0197091 A1 | 8/2012 | Nakano | |
| 2013/0310654 A1 | 11/2013 | Cilibrasi | |
| 2014/0163395 A1 * | 6/2014 | Sapp, Jr. | A61B 5/04085 |
| | | | 600/483 |
| 2014/0228692 A1 * | 8/2014 | Chan | A61B 5/08 |
| | | | 600/484 |
| 2014/0257426 A1 * | 9/2014 | Arcot-Krishnamurthy | |
| | | | A61N 1/36139 |
| | | | 607/44 |
| 2015/0150514 A1 * | 6/2015 | Batchinsky | A61B 5/7275 |
| | | | 600/301 |

OTHER PUBLICATIONS

"Several." Merriam-Webster. Dec. 23, 2013. https://web.archive.org/web/20131223124306/https://www.merriam-webster.com/dictionary/several (Year: 2013).*

Schumann et al. "Bivariate Phase-Rectified Signal Averaging." Physica A: Statistical Mechanics and its Applications, vol. 387, Issue 21, Sep. 1, 2008, pp. 5091-5100. (Year: 2008).*

Masi, et al. "Respiratory Sinus Arrhythmia and Diseases of Aging: Obesity, Diabetes, Mellitus, and Hypertension," Biological Psychology, North-Holldand Pub., Amsterdam, NL, vol. 74, No. 2, Dec. 27, 2006, pp. 212-223.

De Geus, Eco J.C., et al. "Ambulatory Measurement of Respiratory Sinus Arrhythmia and Respiration Rate," Biological Psychology, vo. 41, No. 3, Nov. 1, 1995, pp. 205-227.

Schmidt, Georg et al: "Respiratory Sinus Arrhythmia Predicts Mortality After Myocardial Infarction", Journal of the American College of Cardiology; vol. 63, No. 12, 1 page.

Barthe, Petra. et al. (2013) "Respiratory rate predicts outcome after acute myocardial infarction: a prospective cohort study," as published in European Heart Journal, 34, pp. 1644-1650.

Dommasch, Michael. et al. (2014) "Nocturnal Respiratory Rate Predicts Non-Sudden Cardiac Death in Survivors of Acute Myocardial Infarction," as published in Journal of American College of Cardiology (JACC), vol. 63, Issue 22, pp. 2432-2433.

Sinnecker, Daniel MD "Expiration-Triggered Sinus Arrhythmia Predicts Outcome in Survivors of Acute Myocardial Infarction" Journal of the American College of Cardiology, vol. 67, No. 19, 2016, pp. 2213-2220.

Weinberg, Richard L. MD "Expiration-Triggered Sinus Arrhythmia; Have we Been Waiting With Bated Breath" Journal of the American College of Cardiology, vol. 67, No. 19, 2016, pp. 2221-2223.

* cited by examiner

METHOD AND DEVICE FOR ASSESSING A MORTALITY RISK OF A CARDIAC PATIENT BASED ON RESPIRATORY SINUS ARRHYTHMIA

The present invention relates to cardiology in general and in particular to a method and device for assessing a mortality risk of a cardiac patient such as a post-myocardial infarction patient based on respiratory sinus arrhythmia.

Depending on the outcome of a mortality risk assessment, a specific medical treatment may be administered to the post-myocardial infarction patient. In view of the financial resources available for patients in statutory and private health insurance systems, there is an economical interest in administering specific and costly medical treatment predominantly to those post-myocardial infarction patients who can benefit most from such treatment. Conventional cardiac mortality risk predictors such as LVEF (<35%), Diabetes mellitus, GRACE score (>=120 points) and presence of chronic obstructive pulmonary disease (COPD) are available, but involve considerable efforts for measurement or calculation from patient and health personnel.

Therefore, there is a need for a high reliability mortality risk prediction method and device while minimizing the efforts to be taken by the patient and health personnel as well as the patient's possibility to manipulate the measurement results.

In order to solve the above identified problem, the invention provides, as a first aspect, a method for assessing a mortality risk of a cardiac patient according to claim 1, said method being based on respiratory sinus arrhythmia and comprising the following steps:

Step A: Computing the mean respiratory sinus arrhythmia during inhalation and/or exhalation for a plurality of breathing cycles of said patient.

Step B: Assessing the mortality risk of said patient based on said computation.

Respiratory sinus arrhythmia (RSA) is a naturally occurring variation in heart rate that occurs during a breathing cycle. RSA is also a measure of parasympathetic nervous system activity. During the process of RSA inhalation, vagal activity is temporarily suppressed, causing an immediate increase in heart rate. Exhalation then decreases the heart rate and causes vagal activity to resume. The process of measuring periodic changes in the heart rate during a resting state of cardiovascular activity is known as heart rate variability (HRV).

Now, the inventors of the present invention found that RSA may not only be used as a reference for vagal activity of a patient but also classifies as a reliable mortality risk predictor and is comparably easy to calculate on the basis of standard medical recordings.

On an electrocardiogram (ECG), RSA is seen as subtle changes in the R-R interval (time between two of the distinctive, large, upward "R" spikes on an electrocardiogram) synchronized with respiration. The R-R interval (RRI) on an ECG is shortened during inhalation and prolonged during exhalation.

Typically, RSA decreases with age. However, adults in cardiovascular health are likely to have a more pronounced RSA. Professional athletes typically maintain very high vagal tone and RSA levels. RSA also becomes less prominent in individuals with diabetes and cardiovascular disease. Meditation and relaxed breathing techniques can temporarily alter RSA.

Preferred embodiments are claimed in the subclaims.

According to another aspect of the invention, Step A further comprises at least one of the following sub-steps:

Step A1: Obtaining electrocardiogram recordings of said patient, preferably using an ECG-recorder having X, Y, Z-leads and/or signal resolution of 1.6 kHz and 16 Bit, wherein said electrocardiogram-recordings are more preferably made in digital form, preferably for at least 30 minutes.

Step A2: Identifying QRS-complexes from electrocardiogram-recordings of said patient.

Step A3: Calculating the heartbeat intervals as the periods of time between subsequent two R-peaks of QRS-complexes from electrocardiogram-recordings of said patient.

Step A4: Obtaining a time series representing the respiratory activity or chest movement of said patient, preferably using a piezoelectric chest belt sensor or by high-pass filtering of electrocardiogram-recordings of said patient, wherein time series is preferably obtained in digital form and/or covers a period of time of at least 30 minutes.

Step A5: Determining periodic data points based on said time series for a plurality of breathing cycles of said patient, said data points preferably representing starting times of inhalation and/or exhalation.

Step A6: Identifying the heartbeat interval+matching to at least one of said data points.

Step A7: Calculating a first mean heartbeat interval from at least two consecutive heartbeat intervals prior to at least one of said data points, said first mean heartbeat interval preferably representing a mean heartbeat interval during inhalation or exhalation.

Step A8: Calculating a second mean heartbeat interval from at least two consecutive heartbeat intervals subsequent to the heartbeat intervals used for calculating the first mean heartbeat interval, said second mean heartbeat interval preferably representing a mean heartbeat interval during exhalation or inhalation.

Step A9: Calculating the respiratory sinus arrhythmia for one breathing cycle of said patient by computing a difference and/or a quotient between said first and second heartbeat intervals for at least one of said data points.

Step A10: Calculating mean respiratory sinus arrhythmia of said patient by computing the average of the respiratory sinus arrhythmia according to Step A9 for a plurality of said data points.

According to still another aspect of the invention, Step B further comprises at least one the following sub-steps:

Step B1: Allocating said patient to a low-mortality-risk group in case the mean respiratory sinus arrhythmia calculated for said patient indicates that the heartbeat intervals are decreasing during inhalation and/or increasing during exhalation.

Step B2: Allocating said patient to a high-mortality-risk group in case the mean respiratory sinus arrhythmia calculated for said patient indicates that the heartbeat intervals are stable or increasing during inhalation and/or decreasing during exhalation.

Step B3: Outputting the result of risk stratification based on the results of Step B1 and/or Step B2.

The invention further provides a computer-readable medium containing a program, which, when loaded, performs a method for assessing a mortality risk of a cardiac patient according to one of the preceding aspects.

The invention still further provides a device for assessing a mortality risk of a cardiac patient based on respiratory sinus arrhythmia, said device being configured to perform the method according to one of the preceding aspects.

Further preferred embodiments of the invention result from any possible combination of the features disclosed in the claims, description and drawings,

DETAILED DESCRIPTION OF THE DRAWINGS

FIG. 1 visualizes the principle of high-pass-filtering of an ECG recording of a cardiac patient for obtaining a time series representing respiratory activity of said patient.

Figure 2:
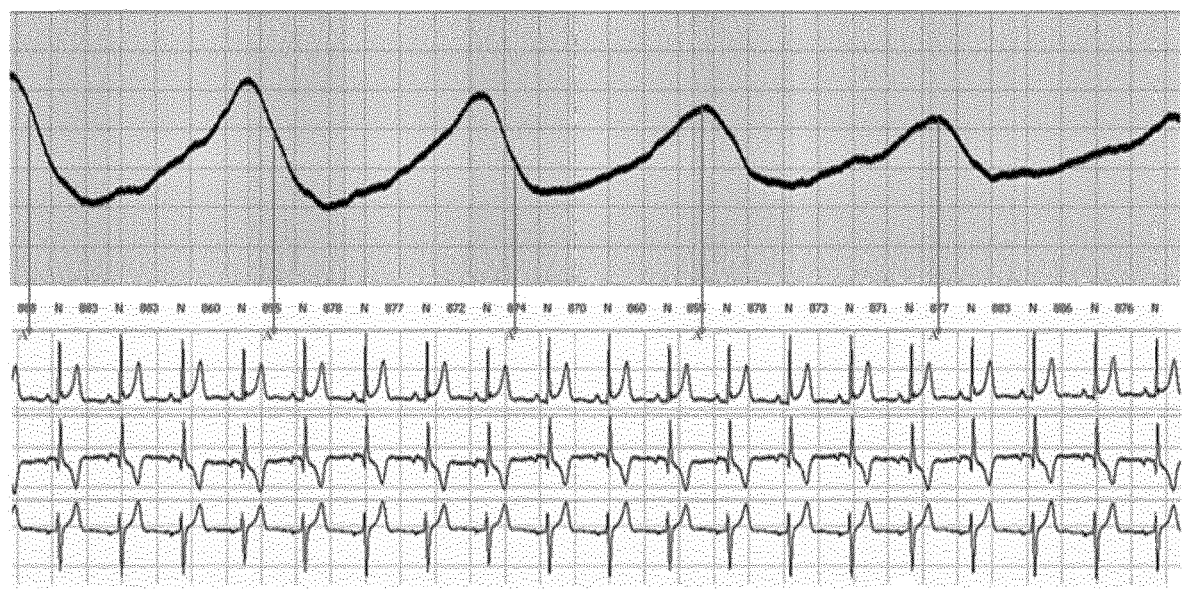

FIG. 2 shows simultaneous recordings of respiratory chest movement (upper tracing) and ECG (lower tracing) for determination of data points representing periodic events during a plurality of breathing cycles of said patient.

Figure 3:
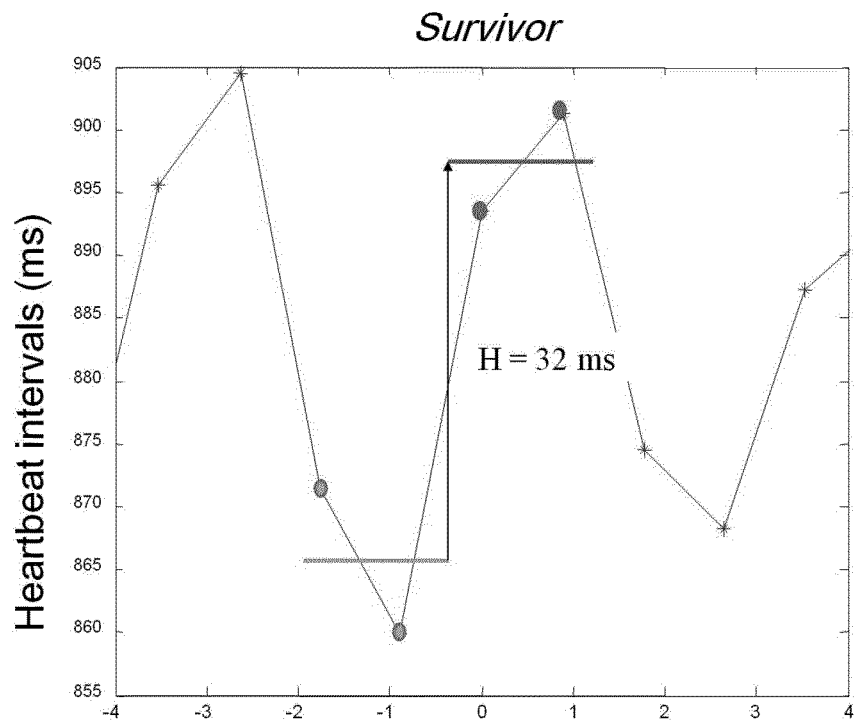

FIG. 3 exemplifies the calculation of the respiratory sinus arrhythmia (RSA) for one breathing cycle of a patient to be allocated to a low-mortality-risk group ("survivor") on the basis of the calculation.

Figure 4:
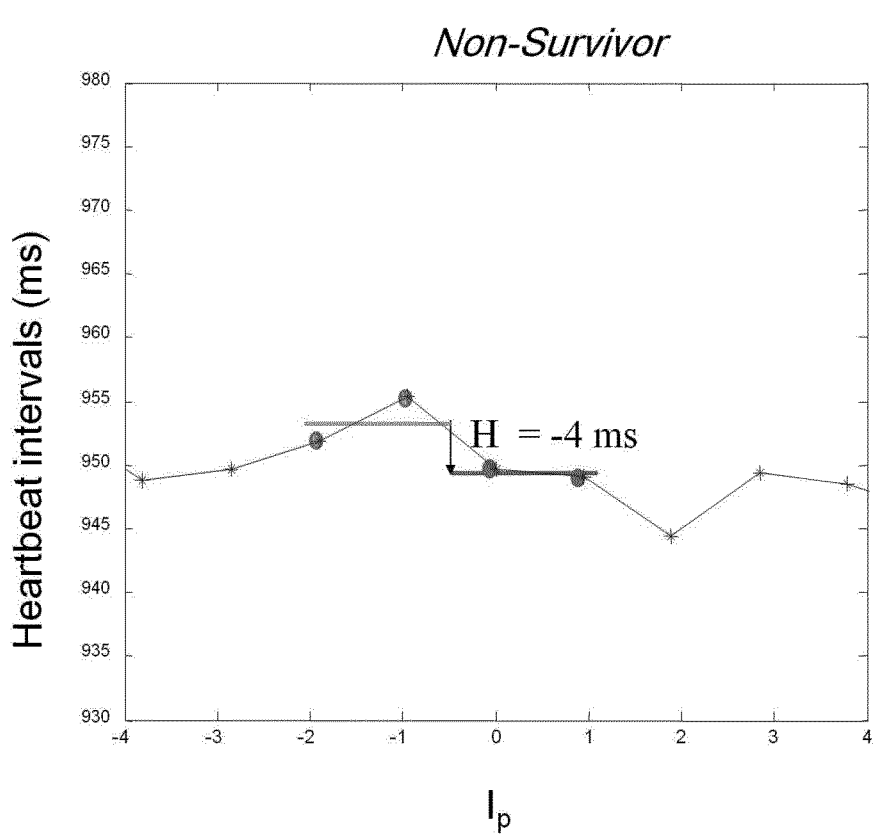

FIG. 4 exemplifies the calculation of the respiratory sinus arrhythmia (RSA) for one breathing cycle of a patient to be allocated to a high-mortality-risk group ("non-survivor") on the basis of the calculation.

Figure 5:
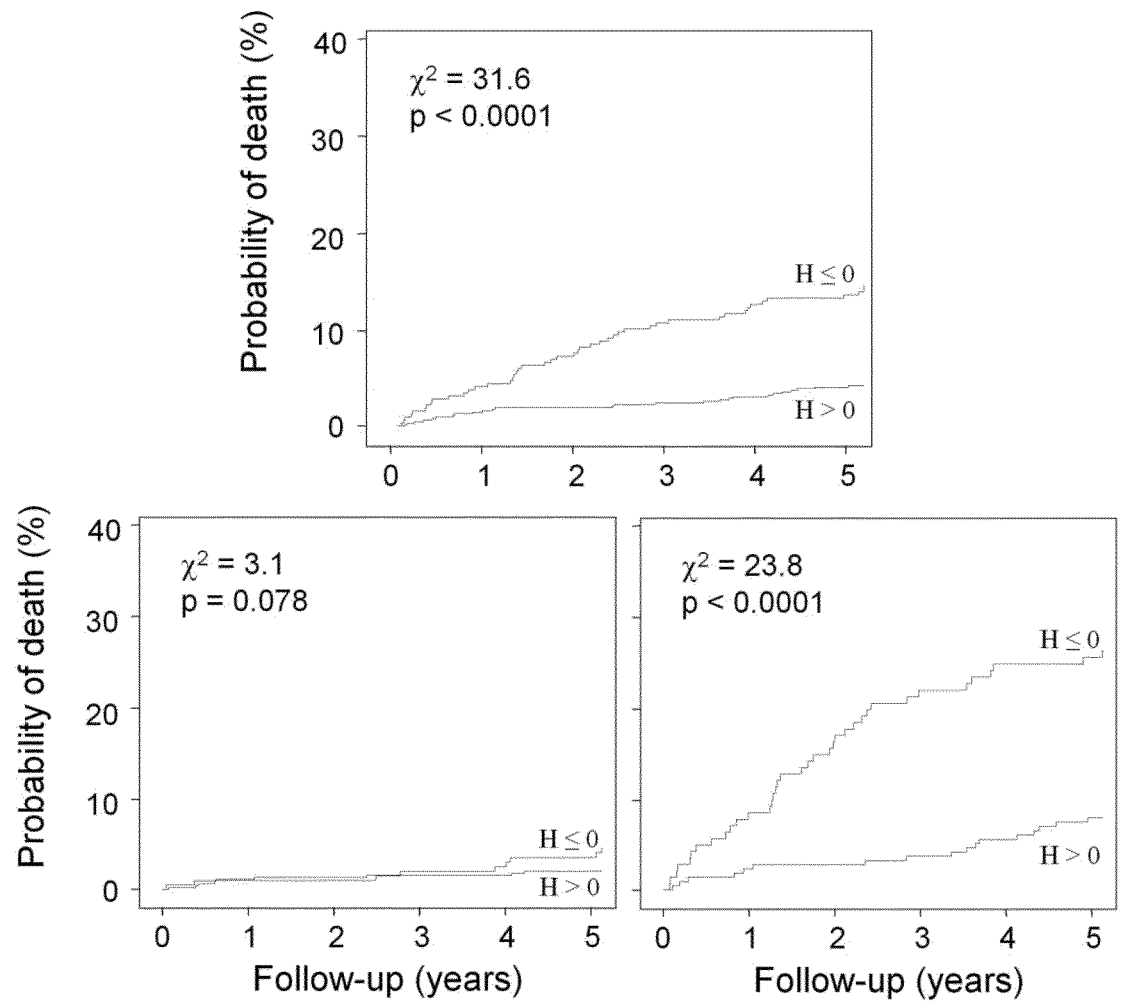

FIG. 5 visualizes mortality risk stratification of a study population by H>0 and ≤0 in all patients (upper panel), in patients with a GRACE score <120 (lower left panel) and in patients with a GRACE score 120 (lower right panel).

DESCRIPTION OF EMBODIMENTS

The preferred embodiment of the invention will now be described with reference to the enclosed drawings:

The preferred method for assessing a mortality risk of a cardiac patient is based on respiratory sinus arrhythmia and is performed using an appropriate device such as a computer. The method comprises the following steps:

In Step A, the mean respiratory sinus arrhythmia during exhalation is computed over a plurality of breathing cycles of said patient. The invention also works with the computation of the mean respiratory sinus arrhythmia during inhalation, however, the computation of the mean respiratory sinus arrhythmia during exhalation is preferred.

Step A involves the following sub-steps:

In Step A1, electrocardiogram (ECG) recordings of said patient are obtained for a period of time of about 30 minutes. ECG recording is usually performed in digital form using a digital ECG-recorder having X, Y, Z-leads, a signal resolution of 1.6 kHz and 16 Bit.

Subsequently, in Step A2, QRS-complexes are identified from said ECG-recordings. The heartbeat intervals are calculated as the periods of time between subsequent two R-peaks of QRS-complexes in Step A3. The data series produced in Steps A2 and A3 contains the time durations of a plurality of consecutive heartbeat intervals detected in said ECG-recordings. If desired, specific data sequences can be selected and/or omitted for further processing in case the ECG-recordings have been interrupted or disturbed or certain data sequences are not useful for other reasons.

Step A4 aims for obtaining a time series representing the respiratory activity of said patient, which can be achieved in various ways. As the patient's respiratory activity is already contained in the electrocardiogram-recordings of said patient, it may be extracted by high-pass filtering of the electrocardiogram-recordings, as disclosed, e.g., by Barthel et al., European Heart Journal, 2013, Dommasch et al., JACC 2014. The muscular contraction of the patient during breathing creates minute electrical potentials which are visible in the EGC recordings. If filtered through a high pass filter, the time series indicating the respiratory activity can be obtained from the EGC recordings as shown in FIG. 1 (lower tracing). Alternatively, a time series representing the respiratory activity of said patient may be digitally recorded using a piezoelectric chest belt sensor. A suitable piezoelectric chest belt sensor is provided by the company Protech. The time series indicates respiratory chest movement. As shown in the upper tracing in FIG. 2, the plotted digital recording of respiratory activity of said patient shows a sinus curve for each breathing cycle with characteristic features during inhalation and exhalation. These characteristic features are taken as a reference for distinction of the different phases of each breathing cycle.

In Step A5, periodic data points for each one of a plurality of breathing cycles of said patient are determined based on said digital time series. Preferably, data points representing the starting times of exhalation are selected. In general, the data points representing the starting times of exhalation are local extreme values of the time series representing the respiratory activity of said patient. The time series representing the respiratory activity basically indicates the lung volume of said patient during respiration. The lung volume is at its maximum at the end of inhalation and is at its minimum at the end of exhalation. Therefore, the transition points between inhalation and exhalation correspond to the local maxima of the time series and the transition points between exhalation and inhalation correspond to the local minima of the time series. Nevertheless, the data points can be defined as desired according to individual needs, Step A6 includes the identification of the heartbeat intervals of said patient matching to or including the data points identified in Step A5, as shown in FIG. 2. The heartbeat interval to be identified is preferably the last complete heartbeat interval, i.e. the heartbeat interval terminated by the last heartbeat prior to the start of exhalation.

Next, as explained with reference to FIGS. 3 and 4, a first mean heartbeat interval is calculated in Step A7 from two consecutive heartbeat intervals prior the (data point indicating the) start of exhalation of one breathing cycle. Therefore, said first mean heartbeat interval basically represents a mean heartbeat interval during inhalation. In the example of FIG. 3, the time duration of the penultimate heartbeat interval prior to the start of exhalation is about 870 ms, and the time duration of the ultimate heartbeat interval prior to the start of exhalation is about 860 ms. Therefore, the first mean heartbeat interval amounts to 865 ms (=(870 ms+860 ms)/2). In the example of FIG. 4, the time duration of the penultimate heartbeat interval prior to the start of exhalation is about 951 ms, and the time duration of the ultimate heartbeat interval prior to the start of exhalation is about 955 ms. The first mean heartbeat interval thus amounts to 953 ms (=(951 ms+955 ms)/2).

Next, as explained with reference to FIGS. 3 and 4, a second mean heartbeat interval is calculated in Step A8 from two consecutive heartbeat intervals subsequent to the heartbeat intervals used for calculation of said first mean heartbeat interval. The second mean heartbeat interval basically represents a mean heartbeat interval during exhalation. In the example of FIG. 3, the time duration of the heartbeat interval during the start of exhalation phase is about 894 ins, arid the time duration of the first complete heartbeat interval after the start of exhalation is about 900 ms. The second mean heartbeat interval thus amounts to 897 ms (=(894 ms+900 ms)/2). In the example of FIG. 4, the time duration of the heartbeat interval during the start of exhalation is about 950 ms, and the time duration of the first heartbeat interval after the start of exhalation is about 948 ms, The second mean heartbeat interval thus amounts to 949 ms (=(950 ms+948 ms)/2).

Next, as explained with continued reference to FIGS. 3 and 4, Step A9 includes calculation of the respiratory sinus arrhythmia (RSA) for one breathing cycle by computing a difference or quotient between said first and second heartbeat intervals. In the example of FIG. 3, the respiratory sinus arrhythmia (RSA) for this particular breathing cycle amounts to +32 ms (=(897 ms−865 ins)) and it is calculated by taking the difference between said first and second heartbeat intervals, in particular by subtracting the time duration of the first heartbeat interval from the time duration of the second heartbeat interval. Alternatively, in the example of FIG. 3, the respiratory sinus arrhythmia (RSA) for this particular breathing cycle may be calculated to 1.04 (rounded) (=897 ms/865 ms) by taking the quotient between said first and second heartbeat intervals, in particular by dividing the time duration of the second heartbeat interval through the time duration of the first heartbeat interval. Both calculations indicate the same physiological reaction, namely that the exhalation decreases heart rate and increases the heartbeat intervals, respectively. In the example of FIG. 4, the respiratory sinus arrhythmia (RSA) for this particular breathing cycle amounts to −4 ms (=(949 ms−953 ms)) and 0.996 (rounded) (=949 ms / 953 ms), respectively, wherein both calculations indicate that the exhalation increases heart rate and decreases the heartbeat intervals. Accordingly, in the example of FIG. 3, it may be concluded that the patient is in cardiovascular health, if the calculated RSA proves to be stable during a plurality of breathing cycles (see Step A10). On the other hand, in the example of FIG. 4, the calculated RSA for one breathing cycle shown indicates that the exhalation increases heart rate and decreases the heartbeat intervals, respectively. Hence, in the example of FIG. 4, it may be concluded that this patient suffers from severe cardiovascular disease, if the calculated RSA proves to he stable during a plurality of breathing cycles (see Step A10).

As mentioned above, the calculation performed in Step A9 is only representative for one breathing cycle. In order to obtain reliable results while eliminating errors due to irregular conditions during ECG and respiration recordings, the assessment of cardiovascular health of the patient should based on the patient's physiological reaction during a plurality of breathing cycles rather than on a single breathing cycle. Therefore, in Step A10, a mean respiratory sinus arrhythmia of said patient is calculated by computing the average of the respiratory sinus arrhythmia over a plurality of breathing cycles of said patient. This is usually done by adding up the calculated RSAs for a plurality of breathing cycles divided by the number of breathing cycles (i.e. the number of added RSAs). The result gives the mean RSA for said patient during exhalation.

The subsequent mortality risk assessment according to Step B is based on the calculation performed in Step A and includes the following sub-steps:

In Step B1, said patient is allocated to a low-mortality-risk group in case the mean respiratory sinus arrhythmia of said patient is calculated to increase during exhalation. This is the case when the mean RSA is greater than 0 (difference) or greater than 1 (quotient). In the example of FIG. 3, RSA calculation of a patient to be allocated to a low-mortality-risk group is exemplified for one breathing cycle. The low-mortality-risk group is also called the group of "survivors".

In Step B2, said patient is allocated to a high-mortality-risk group in case the mean respiratory sinus arrhythmia of said patient is calculated to decrease during exhalation. This is the case when the mean RSA is less than 0 (difference) or less than 1 (quotient). In the example of FIG. 4, RSA calculation of a patient to be allocated to a high-mortality-risk group is exemplified for one breathing cycle. The low-mortality-risk group is also referred to as the group of "non-survivors".

Finally, Step B3 outputs the result of risk stratification based on the results of Step B1 and/or Step B2, preferably on a display of a computer device. An appropriate medical treatment may be administered to the patient depending on the result of the mortality risk assessment using the above method.

Steps A and B and preferably at least one of the sub-steps A1 to A10 and/or B1 to B3, can be implemented using conventional computer devices and software. Therefore, the present invention also relates to a computer-readable medium containing a program, which, when loaded, performs the method for assessing a mortality risk of a cardiac patient described above.

The invention has already been tested in a medical study, as will be explained below:

The aim of the study was to quantify respiratory sinus arrhythmia (RSA) by bivariate phase-rectified signal averaging and to test the novel method as a risk predictor. Clinical and demographic patient characteristics of the medical study are given in Table 1:

TABLE 1

Clinical and demographic patient characteristics

| Clinical data | | Therapy | |
|---|---|---|---|
| Age [years] (median, IQR) | 61 (52-69) | PCI (%) | 93 |
| Female gender (%) | 19 | Thrombolysis (%) | 1.5 |
| Diabetes mellitus (%) | 20 | CABG (%) | 0.6 |
| History of previous MI (%) | 10 | Aspirin (%) | 97 |
| $CK_{max}$ [U/l] (median, IQR) | 1,302 (647-2,465) | β-Blocker (%) | 95 |
| LVEF (%) | 53 (45-60) | ACE inhibitors (%) | 94 |
| 5-year all-cause mortality (%) | 7.7 | Statins (%) | 93 |
| | | Diuretics (%) | 44 |

The medical study involved 30-minute recordings of respiratory chest movements using a piezoelectric chest belt sensor of the company Protech and ECG-recordings with X, Y, Z-leads one week after myocardial infarction (MI), the signal resolution was 1.6 kHz at 16 Bit. Patients were studied in the morning, in a supine resting position whilst on normal medication.

RSA was assessed as H, which was defined as average change of RR interval length of observed around RR intervals that occurred during the exhalation (expiration phase) of the respiratory cycles (FIG. 2). An H 0 was considered abnormal (FIG. 4).

A multivariable analysis included H, the GRACE score, LVEF, and diabetes mellitus. Primary end-point was total mortality at a follow-up period of 5 years.

The results of the medical study can be summarized as follows:

During follow-up, 72 (7.7%) patients died. H was a significant predictor of mortality (upper panel of FIG. 5). In multivariable analysis, H was an independent risk predictor regardless of whether GRACE score, LVEF, and H were used as continuous or as dichotomized variables. H was particularly strong in patients with high GRACE scores (lower panels in FIG. 5). Table 2 gives the results of multivariate Cox-Regression analysis:

TABLE 2

Multivariate Cox-Regression analysis (predefined cut-off values)

|  | Wald | p | Hazard ratio | 95% CI | |
| --- | --- | --- | --- | --- | --- |
|  |  |  |  | Lower | Upper |
| Diabetes | 9.260 | 0.002 | 2.106 | 1.304 | 3.403 |
| LVEF ≤35% | 12.123 | <0.001 | 2.567 | 1.510 | 4.363 |
| GRACE ≥120 | 31.073 | <0.001 | 4.670 | 2.716 | 8.028 |
| H >0 | 19.428 | <0.001 | 2.982 | 1.834 | 4.847 |

Therefore, it can be concluded that H is a promising new risk predictor after acute myocardial infarction. H is independent of standard risk predictors and particularly strong in patients with high GRACE scores.

The invention claimed is:

1. A method for assessing a mortality risk of a cardiac patient based on respiratory sinus arrhythmia and for responding to cardiovascular disease to the cardiac patient based on the assessing of the mortality risk, said method further providing improved reliability of assessing the mortality risk while eliminating errors due to irregular conditions during electrocardiogram (ECG) and respiration recordings, said method comprising:
  computing a mean respiratory sinus arrhythmia during inhalation and exhalation for a plurality of breathing cycles of said patient, wherein computing the mean respiratory sinus arrhythmia comprises:
    obtaining a time series representing a respiratory activity or chest movement of said patient by high-pass filtering of electrocardiogram-recordings of said patient, wherein the time series is obtained in digital form and covers a period of time of several minutes, preferably at least 30 minutes;
    determining periodic data points based on the time series, said periodic data points representing starting times of exhalation;
  computing a respiratory sinus arrhythmia for each breathing cycle by:
    calculating a first mean heartbeat interval from a first set of at least two consecutive heartbeat intervals prior to one of said periodic data points such that a latter one of the at least two consecutive heartbeat intervals in the first set is a last complete heartbeat interval prior to a start of a new exhalation of the patient, the first mean heartbeat interval representing a mean heartbeat interval during inhalation,
    calculating a second mean heartbeat interval from a second set of at least two consecutive heartbeat intervals that are subsequent to the first set, the second mean heartbeat interval representing a mean heartbeat interval during exhalation, and
    determining at least one of:
      (i) a difference between the first mean heartbeat interval and the second mean heartbeat interval by subtracting a time duration of the first mean heartbeat interval from a time duration of the second mean heartbeat interval, wherein a positive difference value corresponds to a first physiological scenario in which exhalation decreases heart rate and increases heartbeat intervals, and a negative difference value corresponds to a second physiological scenario in which exhalation increases heart rate and decreases heartbeat intervals, and
      (ii) a quotient between the first mean heartbeat interval and the second mean heartbeat interval by dividing the time duration of the second mean heartbeat interval through the time duration of the first mean heartbeat interval, wherein a quotient greater than 1 corresponds to the first physiological scenario, and a quotient less than 1 corresponds to the second physiological scenario,
    wherein the difference and the quotient are both representative of the same physiological reaction of the patient, and
  calculating the mean respiratory sinus arrhythmia for the plurality of breathing cycles by calculating an average of the respiratory sinus arrhythmias computed for each breathing cycle;
  assessing the mortality risk of said patient based on the mean respiratory sinus arrhythmia, said assessing comprising:
    allocating said patient to a low-mortality-risk group when the mean respiratory sinus arrhythmia calculated for said patient is a positive difference value or a quotient greater than 1, or
    allocating said patient to a high-mortality-risk group when the mean respiratory sinus arrhythmia calculated for said patient is a negative difference value or a quotient less than 1, and
    outputting the assessed mortality risk; and
  based on allocating the patient to the high-mortality-risk group, determining that the patient suffers from a cardiovascular disease, and selecting a medical treatment for responding to the cardiovascular disease.

2. The method of claim 1, further comprising at least one of the following sub-steps:
  a. obtaining the electrocardiogram recordings of said patient, preferably using an ECG-recorder having X, Y, Z-leads and/or signal resolution of 1.6 kHz and 16 Bit, wherein said electrocardiogram-recordings are more preferably made in digital form, preferably for at least 30 minutes;
  b. identifying QRS-complexes from the electrocardiogram-recordings of said patient;
  c. calculating the heartbeat intervals as being periods of time between subsequent two R-peaks of QRS-complexes from the electrocardiogram-recordings of said patient; and d. the time series is obtained in digital form and covers the period of time of at least 30 minutes.

3. The method of claim 1, wherein the electrocardiogram-recordings of said patient are required to have a signal resolution of 1.6 kHz and 16 Bits.

4. The method of claim 1, wherein the method further includes calculating the first and second mean heartbeat intervals as being periods of time between subsequent two R-peaks of QRS-complexes from the electrocardiogram-recordings of said patient.

5. One or more computer-readable hardware storage device(s) having stored thereon a program, which, when loaded, performs the method for assessing the mortality risk of the cardiac patient according to claim 1.

6. A device for assessing the mortality risk of the cardiac patient based on the respiratory sinus arrhythmia, said device comprising a computer device being configured to perform the method according to claim 1.

7. The device of claim 6, further comprising display means for displaying a result of assessing the mortality risk.

8. One or more computer-readable hardware storage device(s) having stored thereon a program, which, when loaded, performs the method for assessing the mortality risk of the cardiac patient according to claim 2.

9. A device for assessing a mortality risk of a cardiac patient based on respiratory sinus arrhythmia, said device comprising a computer device being configured to perform the method according to claim 2.

* * * * *